United States Patent

Ouchi et al.

[11] 4,351,323
[45] Sep. 28, 1982

[54] CURVABLE PIPE ASSEMBLY IN ENDOSCOPE

[75] Inventors: Teruo Ouchi, Kami-Fukuoka; Hirohisa Ueda, Tokyo, both of Japan

[73] Assignee: Kabushiki Kaisha Medos Kenkyusho, Tokyo, Japan

[21] Appl. No.: 195,735

[22] Filed: Oct. 10, 1980

[30] Foreign Application Priority Data

Oct. 20, 1979 [JP] Japan .................. 54/145299[U]

[51] Int. Cl.³ ............................................. A61B 1/00
[52] U.S. Cl. ....................................... 128/4; 138/120
[58] Field of Search .................. 128/4, 5, 6, 7, 8, 9, 128/349 R; 138/120; 356/241

[56] References Cited

U.S. PATENT DOCUMENTS

| | | | |
|---|---|---|---|
| 3,190,286 | 6/1965 | Stokes | 128/6 |
| 3,557,780 | 1/1971 | Sato | 128/4 |
| 3,583,393 | 6/1971 | Takahashi | 128/4 |
| 3,669,098 | 6/1972 | Takahashi | 128/6 |
| 3,788,304 | 1/1974 | Takahashi | 128/6 |
| 3,799,151 | 3/1974 | Fukaumi et al. | 128/4 |
| 3,998,216 | 12/1976 | Hosono | 128/6 |

Primary Examiner—Lee S. Cohen
Assistant Examiner—Angela D. Sykes
Attorney, Agent, or Firm—Sughrue, Mion, Zinn, Macpeak & Seas

[57] ABSTRACT

A curvable tube assembly for an endoscope which can be inserted through insertion paths of different curvature and along narrow and zigzag paths in a body cavity. First and second curvable tube sections are arranged in succession with one another with each of the first and second curvable sections including a plurality of articulation rings supporting one another at at least two points so as to make the curvable sections bendable in at least two directions. The free end of the second curvable section is connected to a flexible tube. At least one pair of stay coils is provided having ends fastened to the connecting point of the first and second curvable sections. Pull strings are disposed in the stay coils having first ends fastened to the first curvable section and extending to a manual operation unit of the endoscope.

3 Claims, 3 Drawing Figures

CURVABLE PIPE ASSEMBLY IN ENDOSCOPE

BACKGROUND OF THE INVENTION

The present invention relates to a curvable tube which is adapted to be connected to the upper end of a flexible tube of an endoscope and which may be inserted into a body cavity. More particularly, the invention relates to the arrangement of such a curvable tube having a structure with no discontinuous curve at the connecting point of the flexible tube and the curvable tube.

The flexible tube of an endoscope, which is inserted into the body cavity, is connected to a curvable tube assembly and the end of the flexible tube is advanced along a path in the body cavity such as to locate a part to be exmained in the body cavity under observation. In general, the flexible tube is constructed by covering a coarsely wound elastic coil with a cover tube. The flexible tube thus formed suffers from a defect in that it is relatively stiff or curves unevenly against a bending action.

The curvable tube of the prior art is constituted by a number of articulation rings which are juxtaposed by pivotally supporting adjacent articulation rings at two points with the rings covered by a flexible sheath so as to have a swivel articulation function. The curvable tube may be bent in a preferred direction by operating pull strings at the manual operation unit of the endoscope.

In the conventional endoscope, the ends of finely wound non-compressive stay coils provided for the pull strings for bending the curvable tube are fastened to the connecting point of the flexible tube and the curvable tube and an annular relay tube is used to provide a uniform contact surface for the end of the flexible tube having a spiral structure and to connect the two tubes. The relay tube is unbendable. Therefore, when the curvable tube of the tube assembly is bent in the body cavity, because of the presence of the relay tube, a discontinuous curve occurs between the flexible tube and the curvable tube which are bent along the body wall.

Moreover, the conditions of the path in the body cavity along which the end of the tube assembly is passed to reach the part to be examined are not usually uniform. Sometimes the end of the tube assembly must pass along a path which, as in the sigmoid flexure of the large intestine, curves against the direction of insertion of the flexible tube as illustrated in FIG. 1.

When the above-described conventional tube assembly is passed along such a path in a body cavity, specific difficulties are commonly encountered. Specifically, no matter which way the curvable tube 2 is bent, in the range of from the state indicated by the solid line to the state indicated by the chain line in FIG. 1, in a greatly curved and narrow region of an insertion path in a body cavity such as the zigzag path 1 as shown in FIG. 1, it is impossible for the relay tube 3 which forms the discontinuous curve between the curvable tube 2 and the flexible tube 4 to pass smoothly through the region. Therefore, if the flexible tube is inserted under pressure into such a region, the region may be damaged.

The insertion path in a body cavity may include a portion which has a widely varying curvature although not so abrupt as that in the zigzag path shown in FIG. 1. A device in which the active length of a curvable tube can be changed has been proposed to provide a smoothly insertable tube assembly. See, for example, Japanese Published Patent Application No. 35794/1976. The curved portion corresponding to the active length of the curvable tube is uniform in curvature. Therefore, when the curvable tube with a shortened active length is inserted into a short curved path, both ends of the short path are expanded and, when the curvable tube with an elongated active length is inserted a long curved path, the end portion of the curvable tube is merely bent like a hook and cannot be extended satisfactorily along the insertion path. In order to overcome this difficulty, the conventional device is so designed that the front part of the relatively long curvable tube structure is freely bendable in four directions, that is, both horizontally and vertically, while the rear part is bendable only in two directions, that is only one of horizontally and vertically. For this purpose, the front part and the rear part of the curvable tube are made different from each other in the combination of articulation rings forming the curvable tube thereby to control the directions of bending of the swivel articulations.

Although the active length of the curvable tube of the device can be changed as described above, it is impossible for such a curvable tube to smoothly pass through a narrow and zigzag path of the sort shown in FIG. 1 because, even if the curvable tube is curved reversely with its active length shortened, that part is followed by the relatively long part which forms the rear part of the curvable tube and which is controlled to be unbendable.

In view of the above-described difficulties accompanying a conventional tube assembly of an endoscope, an object of the present invention is to provide a curvable tube assembly for an endoscope which can pass through not only insertion paths of different curvature in the body cavity but also narrow and zigzag insertion paths.

SUMMARY OF THE INVENTION

The arrangement of the curvable tube assembly of the invention differs significantly from the conventional assembly in that a second curvable tube is provided which is connected to the active part of a first curvable tube which is externally controllable. The second curvable tube is made of articulation parts similar to the swivel articulation parts of the first curvable pipe assembled in such a manner that the second curvable tube is freely bendable although it cannot be externally positively curved by being limited by stay coils which are provided to control the acting points of pull strings.

More specifically, the invention encompasses a curvable pipe assembly for an endoscope including first and second curvable sections arranged in succession with one another. Each of the first and second curvable sections includes a plurality of articulation rings juxtaposed by pivotally supporting adjacent articulation rings at at least two points so as to be bendable in at least two directions. In a preferred embodiment, each of the first and second curvable sections is bendable in four directions. Preferably also, the articulation rings are supported pivotally at opposite ends thereof along axes which are substantially perpendicular to each other. The free end of the second curvable section is adapted to be connected to a flexible tube. At least one pair of stay coils, which are preferably finely wound, are provided with corresponding pairs of pull strings. The pull strings have first ends fastened to the top of the first curvable section and extend to a manual operation unit of the endoscope. The stay coils have ends fastened to the connecting point of the first and second curvable sections.

DESCRIPTION OF THE PREFERRED EMBODIMENTS

The invention will be described with reference to the accompanying drawings.

Figure 2:
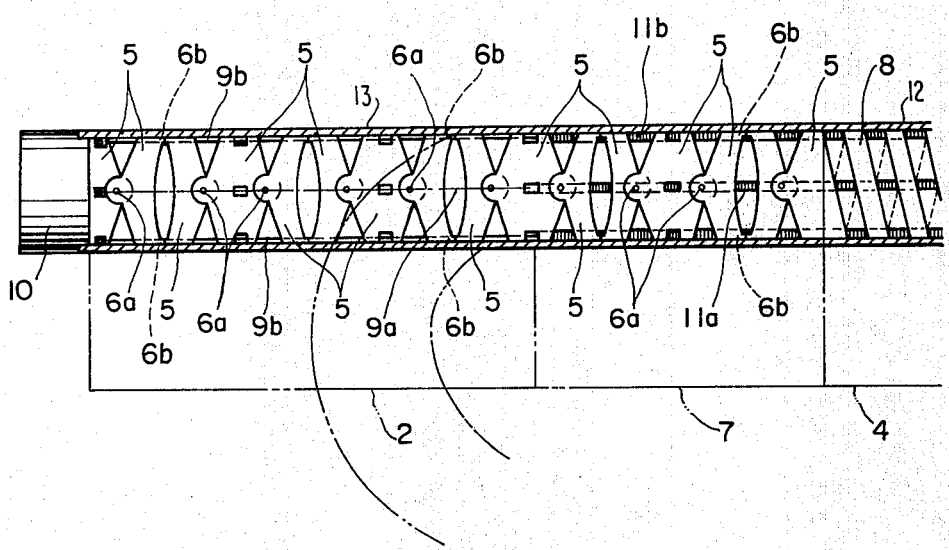
FIG. 2 is a side view, partly as a sectional view, of a preferred embodiment of a curvable tube assembly constructed according to the invention.

FIG. 2 is a side view, partly as a sectional view, showing a preferred embodiment of a curvable tube assembly for an endoscope constructed according to the invention. The curvable tube assembly is constituted by a first curvable tube 2 and a second curvable tube 7 arranged in succession with the first curvable tube 2. Each of the first and second curvable tubes is constituted by an assembly of articulations which is formed by pivotally supporting a number of conventional articulation rings 5 arranged side-by-side. More specifically, adjacent articulation rings 5 are pivotally supported by one another at points 6a and 6b falling along axes perpendicular to each other so that the curvable tubes can be curved or bent in any of four directions. The rear end of the second curvable tube 7 is coupled directly to one end of a flexible tube 4 constructed with a coarsely wound spiral coil 8.

The top or free end of the curvable tube 2 is coupled to a tip end part 10 in which conventional structures of an endoscope scope such as an objective lens window, a forceps withdrawing opening, and air and water delivering openings are provided. The ends of two pairs of pull strings 9a and 9b are fastened to the articulation ring 5 at the top of the tube 2 in such a manner that one pair of pull strings 9a extends along lines connecting the pivotal supporting points 6a while the other pair of pull strings 9b extends along lines connecting the pivotal supporting points 6b. In FIG. 2, reference numeral 12 designates a plastic tube which forms the cover of the flexible pipe and reference numeral 13 designates a highly flexible rubber tube which covers the curvable tube assembly. The pull strings 9a and 9b fastened to the curvable tube 2 are similar in structure to conventional ones. However, it should be noted that, according to the invention, the pull strings 9a and 9b are inserted into finely wound stay coils 11a and 11b, respectively, the ends of which extend to and are fastened to the articulation ring 5 which is located at the top of the second curvable tube 7, that is, at the connecting point of the first and second curvable tubes. The pull strings 9a and 9b and the stay coils 11a and 11b extend through the flexible tube 4 to a curvable tube operation unit in the manual operation section of the endoscope and are connected thereto. The pull strings 9a and 9b thus connected are maintained under a suitable tension.

Similar to the conventional curvable tube, the first curvable tube can be curved in any of four directions, vertically and horizontally, as required by operating the pull strings. In this case, the first curvable tube 2 is curved with substantially the same curvature as indicated by the chain lines in FIG. 2. However, here a part of the flexible pipe 4 is pushed and bent by the wall of the path as a result of which it is deformed to conform to the curvature of the path although the degree of flexibility of the flexible tube is relatively small.

In the second curvable tube 7, between the curvable tube 2 and the flexible tube 4 the structure of the swivel articulations is such that the articulations can be substantially smoothly bent in any of four directions. That is, the second curvable tube 7 is not stiff but is quite bendable.

Figure 1:
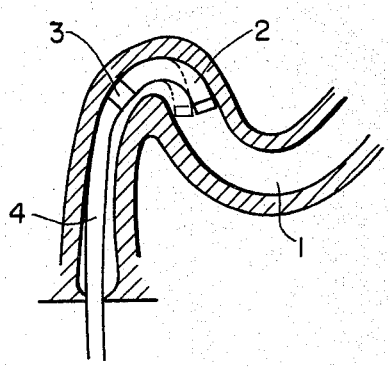
FIG. 1 is a schematic diagram illustrating the insertion of a conventional tube assembly into a body cavity.
Figure 3:
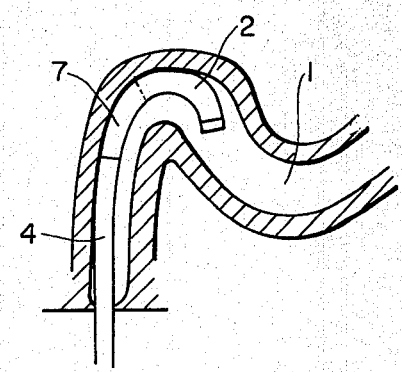
FIG. 3 is a schematic diagram illustrating the insertion of the curvable tube assembly of the invention into a body cavity.

In operation, one of the pull strings 9b is tightened while the other is released by the curvable tube operation unit of the manual operation section of the endoscope. The first curvable tube 2 is bent according to the amount of operation of displacement of the pull strings. The second curvable tube 7 may be further curved by being pressed against the wall of the path or it may be reversely curved depending on the condition of the path. Thus, even in the case of a zigzag path 1 as shown in FIG. 3, the second curvable tube 7 is curved satisfactorily along the path 1 independently of the curve of the first curvable tube 2 which is externally controlled. Accordingly, the operator can insert the second curvable tube 2 into even a narrow and curved path curving the tube exactly along the path. That is, the operator can insert the part of the flexible tube into the body cavity of a person to be examined without damaging the insertion path and inflicting no pain on the patient.

As was described above, the curvable tube assembly of the invention includes a flexible tube, a first curvable tube which can be controlled externally, a second curvable tube provided between the flexible tube and the first curvable tube with the first and second curvable tubes having the same swivel articulation mechanism, and stay coils into which pull strings have been inserted. The stay coils are laid over the second curvable tube as a result of which the second curvable tube has a high flexibility and is not controlled externally. The provision of the second curvable tube eliminates the discontinuous curve between the flexible tube and the first curvable tube. The second curvable tube freely curves along the path without being affected by the external operation. Therefore, similarly to the conventional externally controlled curvable tube the active length of which can be changed, the pipe according to the invention can pass smoothly into paths of different curvatures. Especially, it can pass smoothly along even a narrow and zigzag path.

In the above-described embodiment of a curvable tube assembly of the invention, the curvable tube can freely curve in any of four directions. However, the advantageous effects of the invention can also be obtained by modifying the curvable tube so that it can freely curve in only two directions.

What is claimed is:

1. A curvable pipe assembly for an endoscope comprising:
    a first curvable section having a top end adapted to be coupled to a tip end part of said endoscope;
    a second curvable section arranged in succession with said first curvable section and having a free end;
    each of said first and second curvable sections comprising a plurality of articulation rings juxtaposed by pivotally supporting adjacent articulation rings at points so that said first and second curvable sections are bendable in four directions, the free end of said second curvable section being adapted to be connected to a flexible tube of said endoscope;

two pairs of stay coils located in said second curvable section and having ends fastened to the connecting point of said first and second curvable sections;

two pairs of pull strings disposed in said two pairs of stay coils, said pull strings having first ends fastened to the top end of said first curvable section and said pull strings adapted to extend through said flexible tube to a manual operation unit of said endoscope, movement of said pull strings effecting movement of said first curvable section in said four directions;

said stay coils preventing said movement of said pull strings from moving said second curvable section in any of said four directions.

2. The curvable pipe assembly for an endoscope of claim 1 wherein said stay coils are finely wound.

3. The curvable pipe assembly for an endoscope of claim 1 wherein said articulation rings are pivotally supported at opposite ends thereof along substantially perpendicular axes.

* * * * *